(12) United States Patent
Tanghoej et al.

(10) Patent No.: US 8,282,624 B2
(45) Date of Patent: *Oct. 9, 2012

(54) URINARY CATHETER ASSEMBLY ALLOWING FOR NON-CONTAMINATED INSERTION OF THE CATHETER INTO A URINARY CANAL

(75) Inventors: Allan Tanghoej, Kokkedal (DK); Lars Boegelund Jensen, Roedovre (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/037,378

(22) Filed: Mar. 1, 2011

(65) Prior Publication Data

US 2011/0147238 A1 Jun. 23, 2011

Related U.S. Application Data

(63) Continuation of application No. 12/003,230, filed on Dec. 20, 2007, now Pat. No. 7,922,712, which is a continuation of application No. 10/026,819, filed on Dec. 27, 2001, now Pat. No. 7,311,698.

(30) Foreign Application Priority Data

Sep. 24, 2001 (DK) ................................ 2001 01386

(51) Int. Cl.
*A61F 5/44* (2006.01)
*A61M 27/00* (2006.01)
*A61M 5/32* (2006.01)

(52) U.S. Cl. .......................... 604/544; 604/349; 604/163
(58) Field of Classification Search .................. 604/544, 604/39–42, 171, 172, 265, 327–331, 349–350, 604/165.01, 163.27
See application file for complete search history.

(56) References Cited

U.S. PATENT DOCUMENTS

| | | | | | |
|---|---|---|---|---|---|
| 3,154,080 | A | * | 10/1964 | Rowan et al. | 604/171 |
| 3,648,704 | A | * | 3/1972 | Jackson | 604/172 |
| 4,248,909 | A | * | 2/1981 | Whittaker | 427/162 |
| 5,041,085 | A | * | 8/1991 | Osborne et al. | 604/541 |
| 6,004,305 | A | * | 12/1999 | Hursman et al. | 604/328 |
| 6,578,709 | B1 | * | 6/2003 | Kavanagh et al. | 206/364 |
| 6,634,498 | B2 | * | 10/2003 | Kayerød et al. | 206/364 |
| 7,311,698 | B2 | * | 12/2007 | Tanghoj et al. | 604/544 |
| 7,517,343 | B2 | * | 4/2009 | Tanghoj et al. | 604/544 |

* cited by examiner

*Primary Examiner* — Kevin C Sirmons
*Assistant Examiner* — Andrew Gilbert
(74) *Attorney, Agent, or Firm* — Coloplast Corp., Coloplast A/S; Daniel G. Chapik; Nicholas R. Baumann (57) ABSTRACT

A catheter assembly allowing for non-contaminated insertion of the catheter into the urinary canal. The catheter assembly includes a urinary catheter, a catheter package and a sealing member. The urinary catheter defines a conduit and has a proximal end adapted for insertion into the urinary canal and an opposite distal end. The catheter package has a hose with a cavity for accommodation of the catheter, and a catheter outlet adapted to dismantle the proximal end of the catheter from the catheter package. The sealing member is adapted to provide a substantially liquid-tight seal between the catheter package and the urinary catheter while the catheter is being dismantled.

15 Claims, 11 Drawing Sheets

URINARY CATHETER ASSEMBLY ALLOWING FOR NON-CONTAMINATED INSERTION OF THE CATHETER INTO A URINARY CANAL

RELATED APPLICATIONS

This application is a continuation of application Ser. No. 12/003,230, filed Dec. 20, 2007 and issuing as U.S. Pat. No. 7,922,712 on Apr. 13, 2011, which is a continuation of application Ser. No. 10/026,819, filed Dec. 27, 2001 and issuing as U.S. Pat. No. 7,311,698 on Dec. 25, 2007, and hereby claims the priority thereof to which it is entitled.

FIELD OF THE INVENTION

The present invention relates to a urinary catheter assembly comprising a package allowing for storage of the catheter and for contamination free insertion of the catheter into a natural or an artificial urinary canal of an individual.

BACKGROUND OF THE INVENTION

Catheters for draining the bladder are increasingly used for intermittent as well as indwelling or permanent catheterisation. Typically catheters are used by patients suffering from urinary incontinence or by disabled individuals like para- or tetraplegics who may have no control permit voluntary urination and for whom catheterisation may be the way of urinating e.g. permitting the individual to stay seated in a wheel chair or lying in bed.

Typically, catheters are provided to the user enveloped in a completely sealed and sterilised package. During use and prior to insertion, the catheter is typically removed completely from the package whereby a potential contamination of the catheter may occur, e.g. if the user unintentionally touches the catheter or if the catheter touches surrounding obstacles, toilet seat, wash basin etc. Catheter packages and assemblies of catheters and packages exist, wherein both a proximal end and a distal end of the package may be opened, thus allowing for draining the urine through a catheter which is still at least partly enveloped in the package. Thereby, the user may urinate without completely exposing the catheter and the risk of contamination is reduced. However, since there is a clearance between the inner surface of the catheter package and the outer surface of the catheter itself, urine may flow backwards in the package in a direction opposite to the flow direction inside the catheter. An unwanted situation is that the user of the catheter and/or the surroundings gets contaminated by urine or other liquid substances, e.g. a lubricant or water applied to the catheter for the purpose of reducing the surface friction.

Since only the inserted part of the catheter is exposed from one end of the package prior to insertion of the catheter, another unwanted situation may be that the user unintended forgets to open the other end of the catheter package. An amount of urine may thereby build up in the catheter package and possibly cause a back-flow in the catheter tube. In this case there is a risk of severe contamination of the surroundings and also a possibility of back-flow into the bladder.

Moreover, existing catheters are provided in various sizes. As an example, catheters, which are relatively long, are offered for male individuals whereas relatively short catheters are offered for female individuals. The at least two variants, imply problems and costs for the providers of urinary catheters.

Catheter assemblies comprising a catheter and a package which includes an amount of a liquid substance, e.g. a lubricant for a conventional catheter or a liquid swelling medium for a hydrophilic catheter, exist. Some of the existing packages provide a combination between a storage volume for sterile storage of the catheter and a reservoir for collection of liquid substances, e.g. for collection of friction reducing substances or for collection of urine. Typically there is a large disproportion of the storage capacity necessary for storing the friction-reducing substance and the urine, respectively. Accordingly, the known catheter assemblies of this kind are provided with a relatively small storage container for storing the friction-reducing substance inside the relatively large urine reservoir. It is a disadvantage of the known assemblies that the user, prior to insertion of the catheter into the urinary canal, will have to rupture the storage container in order to achieve a reduced surface friction of the catheter. Especially, it is a disadvantage in the event that the catheter is a hydrophilic-coated catheter. In this event, the user would need to open the storage container to allow a liquid swelling medium stored therein to activate the coating and then wait for at least 30 seconds in order to complete the activation prior to insertion of the catheter.

DESCRIPTION OF THE INVENTION

It is an object of the present invention to overcome the above-described disadvantages of the known catheter assemblies by providing a urinary catheter assembly which, according to a first aspect of the invention, allows for non contaminated insertion of a catheter into a urinary canal, said assembly comprising a urinary catheter defining a conduit and having a proximal end adapted for insertion into a urinary canal of an individual and an opposite distal end, and a catheter package having a generally tubular body such as a hose with a cavity for accommodation of the catheter. The proximal end of the package includes a catheter outlet through which the proximal end of the catheter can be "dismantled" or projected from the catheter package upon opening thereof. The assembly further includes sealing means adapted to provide a substantially liquid tight seal between the catheter package and the urinary catheter, while the catheter is being dismantled or projected from the package.

The sealing means may be provided in the proximal end of the package, e.g. constituting a closure for the proximal end of the package. As an example, the closure may have a rupturable portion with a shape which matches the outer cross-sectional shape of the catheter. When the catheter is removed through the rupturable portion, the closure will sealingly surround the catheter while the catheter is being dismantled. The cavity is thereby defining a receptacle between the catheter and the hose. The receptacle may e.g. be used for storage of a friction-reducing substance.

The sealing means may also be arranged between an outer surface of the urinary catheter and an inner surface of the hose. As an example, the sealing means may be provided in the form of a sliding seal adapted to move in relation to either one of the inner surface of the hose, the outer surface of the catheter or both, while still providing a substantial liquid tight passage therein between. The cavity thereby defines an upper receptacle located near the proximal end of the package and an oppositely located lower receptacle between the catheter and the hose. Especially the upper receptacle may advantageously be used for storing a friction reducing substance for treatment of at least the proximal end of the catheter in the package.

The catheter or at least a part of the catheter could be made from silicone or from a thermoplastic elatomeric material, other thermoplastic materials, curable elastomeric materials, polyamide resins or elastomers or any mixture thereof, i.e. the group may comprise materials like, PVC, PU, PE, latex, and/or Kraton™.

Preferably the catheter is provided with a bending moment defined as the product between E-modulus and moment of inertia of at least 1 MPamm$^4$.

Since the proximal (insertable) end of the catheter, for male individuals, must pass prostate in a curved passage, the proximal end portion of the catheter, e.g. the first 10-50 mm. such as 20-40 mm., such as 25-35 mm, such as the first 30 mm. of the catheter may be provided with an even lower bending moment defined as the product between E-modulus and moment of inertia of less than e.g. 0.6 MPamm$^4$ or even less than 0.3 MPamm$^4$. Other parts of the catheter, e.g. a distal end portion where the urine is drained into the toilet, a bag or place of disposal, may similarly be provided with a different bending moment.

The cross-sectional flow area or the hydraulic radius defined as the ratio of the cross-sectional flow area to the wetted perimeter, may be selected independently upon the length, e.g. on the basis of the size of the urinary canal, which size preferably differs between the individuals.

Preferably, the catheter is provided in an insertable length in the range of 50-90 mm., such as in the range of 55-85 mm., such as in the range of 60-80 mm. such as with a length in the size of 70 mm. which length has been found to be a suitable insertable length for most female individuals. For male individuals, the insertable length of the catheter may preferably be provided in the range of 180-250 mm., such as in the range of 190-240 mm., such as in the range of 200-230 mm. such as in the size of 220 mm. For the male individuals it may further be preferred to provide at least a part of the inserted end of the catheter in a material or in dimensions so that a the tube becomes very flexible in order to easy the passage of the catheter past prostate.

The inner cross-sectional shape of the catheter should preferably be substantially circular with a cross-sectional area in the range of 0.5 mm$^2$-50 mm$^2$.

The outer cross-sectional shape and size of the catheter should be provided with regards to the size of the urinary canal and/or the passage into the bladder so that the catheter around the outer surface thereof seals liquid-tightly.

The catheter or at least a section thereof may be provided with a hydrophilic surface. When treated with a liquid swelling medium, such a surface will provide an excellent lubrication for the insertion and also provide compatibility with the body tissue.

However, the catheter may also be of the traditional type wherein the low friction character is obtained by application of a lubricant different from water, e.g. a silicone based lubricant, the lubricant being applied to at least a section of the catheter.

The liquid swelling medium for a hydrophilic surface may be provided in the package, especially in the upperstorage compartment, near the proximal end of the catheter, when the catheter is arranged in the package. Thereby, the low friction character will be initiated already when the catheter is being arranged in the package. The liquid swelling medium may simply be a saline solution, a bactericidal solution capable of swelling the hydrophilic surface and capable of keeping the surface in a sterile condition or it may be any suitable liquid swelling medium. The swelling may also be initiated already before packaging of the catheter, the catheter then being packed in a substantially gas impermeable package for conservation of the moistened surface. Furthermore, the liquid swelling medium may be provided in a capsule or container directly within the hose member together with the catheter for swelling of the hydrophilic material immediately prior to the insertion.

It is an advantage to provide the catheter package in a material which is at least substantially gas and water impermeable, which is durable to at least moderate external conditions, such as temperature variations and light. The material should at least substantially maintain its properties over a period of up to 12 or more months, e.g. up to 24 month. The catheter package and/or the hose member could therefore preferably be made from silicone or a thermoplastic elastomeric material, other thermoplastic materials, curable elastomeric materials, polyamide resins or elastomers or any mixture thereof, i.e. the group may comprise materials like, PA, PP, PVC, PU, PE, latex, and/or Kraton™. All parts of the catheter package may be made from two foils of a sheet material joined along edges, e.g. by melting or gluing the foils together or she package may be made from an extruded substantially tubular member being closed in both ends. The foil may advantageously be made from laminates of different materials. One layer may e.g. be a layer of aluminium or similar metal for provision of a completely gas-impermeable package.

The proximal end and the distal end of the catheter package could be provided with an even structure. However, it will be preferred that the proximal end of the package is provided with opening means adapted to remove the proximal end of the catheter. Similarly, the distal end of the may be provided with opening means adapted specifically for draining fluid substances from the package. The fluid substances may either be a friction-reducing medium or urine.

Preferably, the hose member is an elongate and/or tubular member adapted to accommodate at least a major part of the catheter. If the catheter is of the kind which develops a low friction surface character upon treatment with a liquid medium or substance, it may be an advantage to provide the liquid medium in the package and preferably in the hose member. The catheter will thereby be treated already upon removal of the catheter from the package. For this purpose, the hose member may preferably be adapted to relatively closely enclose the catheter. As an example, the inner diameter of the hose member may preferably be in the range of 1.1-2 times the outer diameter of the catheter, such as 1.2-1.9 times, such as 1.3-1.8, such as 1.4-1.7, such as 1.5-1.6, such as in the size of 1.55 times the outer diameter of the catheter. Alternatively, the liquid medium may be contained in a pouch connected to the package. The pouch may e.g. constitute a closure for closing either the proximal or the distal end of the package. Preferably, the pouch is integrated in a closure for closing the proximal end of the package, which end is located near the proximal end of the catheter.

If the catheter is a hydrophilic catheter, i.e. if the catheter is either coated with a hydrophilic coating or made completely from a hydrophilic material, the liquid substance may be water or a water/saline solution. If the catheter is of the traditional type having a primarily hydrophobic surface, the liquid substance may be a lubricant, e.g. based on silicone.

The sealing means could be provided in the form of an obstruction which substantially prevents a liquid, substance to pass between the inner surface of the package and outer surface of the catheter. The sealing means thus divides the space confined between the catheter and the hose member into an upper receptacle, in the direction towards the proximal end of the catheter and package and a lower receptacle, in the direction towards the distal end of the catheter and package.

As an example, the sealing means could be provided as a radially outwardly extending protrusion of the outer surface of the catheter or as an inwardly extending protrusion of the inner surface of the hose member, e.g. in the form of a resilient vane adapted to contact the inner surface of the hose member or outer surface of the catheter, respectively. The outwardly extending protrusion of the catheter should in this respect be understood either as a protrusion connected to the catheter or a protrusion formed directly on the surface of the catheter. As an example, the catheter may be connected with a plug member, which plug member is provided with vanes adapted to slide along the inner surface of the hose or at least parts thereof. Similarly, the inwardly extending protrusion of the hose should be understood either as a protrusion connected to the hose or a protrusion formed directly on the inner surface thereof.

Two more radially outwardly or inwardly extending protrusions of the outer or inner surfaces of the catheter and/or the hose member, will provide an even better sealing against flow of liquid substances between the two compartments. By providing the at least two radially inwardly extending protrusions of the inner surface of the hose member with different radial sizes, a further sealing effect will be achieved.

According to a preferred embodiment, the sealing means comprises a ring shaped member arranged between the inner surface of the hose member and the outer surface of the catheter. As an example, a regular ring-shaped gasket may be placed inside the hose member. Preferably, the member is loosely arranged so that it is allowed to move back and forth inside the hose. As an example, the ring shaped member may be provided with a clearance against the hose member and against the catheter so that liquid substances are substantially prevented from passing the ring shaped member and so that the ring shaped member is still allowed to be shifted longitudinally back and forth in the catheter package.

The ring shaped member may preferably be adapted to co-operate with an inwardly extending protrusion of the inner surface of the hose member or with an outwardly extending protrusion of the catheter.

The distance from the distal end of the urinary catheter to the position of the sealing means may preferably be provided between 0 and 100% of the total distance between the distal end of the catheter and the proximal end of the catheter, such as 0%, such as 10%, such as 20%, such as 30%, such as 40%, such as 50%, such as 60%, such as 70%, such as 80%, such as 90%, such as 99%.

In general, the problems of introducing a catheter into the urethra depend not only of the size of the introduced part of the catheter but also on the slipperiness of the introduced part. As previously mentioned, the catheter or at least a part of the catheter adapted for insertion into the urethra or an artificial urinary canal may often be provided with a surface slipperiness for easy and safe insertion. However, it has been found that the slippery surfaces are difficult to handle, not least for a user having reduced dexterity. It is therefore an important aspect of the present invention to allow the user to manipulate the catheter by touching only the catheter package and only to "dismantle" or expose a length of the catheter which is necessary for opening the bladder. Preferably, the sealing means is arranged so as to seal between the outer surface of the catheter and the inner surface of the hose over a certain dismantling or projecting length. This will allow the user of the catheter to withdraw the catheter at least partly from the package, e.g. by pulling the proximal end of the catheter out of the catheter package, meanwhile the sealing between the catheter and the package remains. The feature allows that a catheter type of one length can be supplied both to male and female users. The user only needs to withdraw a length of the catheter from the catheter package necessary for opening the bladder, i.e. approximately 50-90 mm, for female users and approximately 180-250 mm. for male users.

The sealing means and/or the hose member may preferably be provided so that a passage between the outer surface of the catheter and the inner surface of the hose member remains sealed while the catheter is being dismantled or projected from the package over a first dismantle period, thus preventing fluid from passing between the urinary catheter and the hose member when the sealing means is positioned within said first period.

In order not to contaminate the surroundings with friction-reducing substances, it is an advantage to allow such a substances which may possibly be stored in the upper receptacle to drain down into the lower receptacle before dismantling or projecting the catheter through the proximal end of the package. The sealing means and/or the hose may therefore preferably be provided so that a clearance is defined between the outer surface of the urinary catheter and the inner surface of the hose member over a second dismantling period, thus allowing a fluid to pass between the urinary catheter and the hose member when the sealing means is positioned within said second period. As the catheter is being removed from the package, the catheter enters the second dismantling period. Any liquid substance contained in the upper receptacle is thereby drained down into the lower receptacle and it is thereby avoided that the substance might otherwise be unfortunately released though the proximal end of the package.

The length of the first dismantling period may preferably constitute between 0 and 100% of a total length of the package, such as 0%, such as 10%, such as 20%, such as 30%, such as 40%, such as 50%, such as 60%, such as 70%, such as 80%, such as 90% or such as 100%.

According to one embodiment, the substantially liquid tight seal is provided continuously between the catheter package and the catheter over the first dismantle period. However, the liquid tight seal may also be provided discontinuously.

Most catheters are provided with a surface which, when treated with a friction-reducing substance, exhibits a low friction surface character. Accordingly, it is an advantage that the package defines a liquid sight wetting pocket for treatment of the surface part with such substances. In the case that the catheter is hydrophilic or at least is provided with a hydrophilic surface coating on at least the proximal end thereof, the substance would typically be a water based solution, e.g. a saline solution. If the catheter is not hydrophilic, the substance may e.g. be a silicone based solution.

It is a further advantage to provide the assembly with an amount of the substance which is sufficient for effecting a treatment of at least a part of the catheter surface. As an example, the treatment may be performed on a first part of the catheter, which part is adapted for insertion into the urethra. The treatment may advantageously take place in the upper receptacle.

According to a preferred embodiment of the invention, the substance is contained in a pouch connected to the assembly. The pouch may as an example constitute a closure for closing one of either the proximal or distal ends of the package, which end is preferably the proximal end of one package which end is located near the proximal end of the catheter. According to another preferred embodiment, the substance is applied to the receptacle or at least the upper receptacle during the assembling process. The low friction surface character of the catheter is thereby initiated already from the time when the catheter assembly is produced. The package is therefore preferably formed with a wall of a substantially gas impermeable material so as to allow long time preservation of the catheter and a liquid substance in the package.

It is an advantage to provide the package with an opening for draining a liquid substance out of the package. As an example, the opening may be used for draining out surplus liquid swelling medium remaining in the package after treating a hydrophilic catheter. As another example, the opening may be used for draining urine out of the package. For this purpose, the opening is preferably provided in the distal end of the package. During use, the individual may simply have to withdraw a length of the catheter which is sufficient for causing the urine to flow from the bladder. The urine will flow through the catheter conduit and into the package. The urine is allowed to drain out of the package, e.g. into the toilet or into a collection bag or reservoir connected to the package, through the opening. Preferably the opening is closed by closing means connected to the catheter for causing opening of the package upon removal of the catheter from the package. As an example, the opening may closed by the distal end of the catheter itself.

According to a preferred embodiment of the invention, the closing means connected to the urinary catheter is provided with a flow channel co-operating with an outlet provided in the package. In a first position of the closing means in relation to the outlet, liquid substances are allowed to flow from the conduit of the catheter and out of the package. In another position, liquid substance are prevented to flow from the conduit of the catheter and out of the package. The two positions corresponding to a catheter respectively taken out of the package or being taken out of the package and a catheter arranged in the package.

The flow channel of the closing means may further comprise at least one inlet allowing a liquid substance to flow between the one of either the lower or upper storage compartments and the conduit of the catheter. In order to prevent urine, drained through the catheter, from running out through the inlet, the inlet may be provided with means adapted to allow a liquid substance only to flow in the direction from one of either the lower or upper storage compartments and into the conduit.

Preferably, the hose is formed with a wall of a flexible material so as to allow the hose wall to be squeezed into contact with the catheter by finger pressure. This will allow a user of the assembly to use the hose as an applicator for guided non-contaminating insertion of the catheter into the urinary canal. For that purpose, it is an advantage to provide the hose so that the user may vary the length of the hose. This will allow the user to contract the hose for exposing the proximal end of the catheter through the catheter outlet.

The variable length may be provided by a telescopic arrangement of a first part of the hose in relation to a second part of the hose or it may be provided via a concertina folded wall part of the hose.

The package may preferably be closed, in the proximal end by a detachable closure, e.g. by a thin foil glued onto an opening of the proximal end of the package. This will allow the user to open the proximal end of the package by pushing the proximal end of the catheter though the foil, thereby letting the foil be penetrated by the catheter tip.

According to a preferred embodiment, the catheter assembly is provided with a compartment being closed in a first end whereas in a second opposite end it is detachably connected with the hose member. The compartment may preferably be formed with a wall of a flexible material allowing the compartment wall to be squeezed into contact with the catheter by finger pressure. Thereby, the compartment may be used as an applicator for guided non-contaminating insertion of the catheter into the urethra after opening the first closed end and detachment of the compartment from the hose member. The compartment may preferably be tubular and preferably, the hose member and compartment in combination forms a tubular member of a length which allows for accommodation of at least a mayor part of the catheter. Preferably, the catheter is arranged inside the package so that it extends from the hose member and into the compartment. Thereby, the user may grip the proximal end of the catheter by squeezing the compartment into contact with this part of the catheter and, upon detachment of the compartment from the hose member, insert the catheter into the urethra.

A detachable cover member may preferably close the other end of the compartment. After removal of the cover member, the user may draw the proximal catheter end out of the compartment, e.g. by squeezing the compartment into contact with the catheter, withdrawing a piece of the catheter from the hose member, releasing the squeezing grip of the compartment and by moving the compartment down to a part of the catheter now layed open from the hose member. For this purpose, it is an advantage to provide at least a first part of the hose member with a wall of a flexible material so as to allow the first part of the hose wall to be squeezed into contact with the catheter by finger pressure. Thereby, the user can hold the catheter through the compartment wall while the catheter is moved out of the hose member and then hold the catheter through the hose member wall, while the compartment is moved down to a part of the catheter now being exposed. At this point, the compartment may be used for holding the catheter while the catheter is inserted into the urethra. Only a certain length needed for the opening of the bladder is withdrawn from the hose member while the other part of the catheter remains inside the hose member. So as to avoid contamination of the surroundings, the detachable cover member may preferably be provided so that it can be re-connected the compartment after catheterisation, thus leaving at least the proximal end of the package closed.

In order to facilitate coordinated operation of the hose member and the compartment for non-contaminated insertion of the catheter into the urethra, at least a first part of the hose member and preferably the part enveloping the proximal end of the catheter, may be formed with a concertina folded wall. This will allow the length of the hose wall to be extended and shortened respectively which again will facilitate easy removal of the proximal end of the catheter from the hose member. As an example, the proximal end of the catheter may be enveloped in the hose member. In order to be able to squeeze the compartment into contact with the catheter, the user will first have to move the catheter out of the hose member and into the compartment. With the concertina folded wall of the hose member, the user may simply press the compartment against the concertina folded hose member. The length of the hose member is thereby being reduced and the proximal end of the catheter is moved into the compartment. The user may now grip the catheter through the compartment wall and thus pull the proximal end of the catheter out of the catheter package without touching and possibly contaminating the catheter.

In order to provide a catheter assembly which is uncomplicated to use even for persons with a reduced dexterity, the compartment, the cover member and/or at least a part of the hose member may be provided with a gripping zone for easing the grip during use of the compartment for insertion of the catheter into the urethra.

The gripping means may be provided as a radially extending flange or flanges of the compartment, cover member and/or the hose member or as a zone or zones of the compartment, cover member and/or the hose member having a large outer cross sectional diameter. The compartment, cover member and/or the hose member may also be provided with means for engaging an external handle. As an example, the compartment, the cover member and/or the hose member may be provided with a ring-shaped bulge for attaching a handle.

The connection between the compartment and the hose member may preferably be provided by a weakening line for tearing off the compartment from the hose member.

The connection between the second compartment and the hose member may be provided so that the connection can be re-established by twisting and/or pushing the second compartment onto the hose member.

The second compartment may be provided with a weakening line for opening the first end by tearing off a first end part of the compartment.

For disabled users there may be severe difficulties in entering available toilet rooms. It is therefore an advantage to make the use of the catheter totally independent of the availability of toilet rooms by connecting a distal end of the package with a reservoir for accommodation of a liquid substance. In this case, the catheter package or at least the hose member thereof, may even be integrated in the reservoir.

It is an advantage to provide the reservoir in a material which is durable to at least moderate filling with a liquid without causing destruction of the reservoir or evaporation of the liquid substance through the walls of the reservoir. Moreover, the walls of the reservoir should at least substantially maintain its properties over a period of up to 12 or more month, e.g. up to 24 month. The reservoir could therefore preferably be made from a thermoplastic elastomeric material, other thermoplastic materials, curable elastomeric materials, polyamide resins or elastomers or any mixture thereof, i.e. the group may comprise materials like, PA, PP, PVC, PU, PE, latex, and/or Kraton™. Preferably, the reservoir is made from two foils of a sheet material joined along edges, e.g. by melting or gluing the foils together. The foils may e.g. be laminated from various materials and may e.g. comprise one layer of aluminium or a similarly metallic layer for providing a completely gas impermeable package.

It is an advantage if the reservoir is provided with a volume so that it will never be filled to its limit. Accordingly, the reservoir may preferably be provided with a volume in the range of 500-5000 ml, such as 600 ml, such as 700, such as 800, such as 900 ml, such as 1000, such as 1500 ml, such as 2000, such as 2500, such as 3000 ml, such as 3500, such as 4000 ml, such as 4500, such as 5000.

It is an advantage if the liquid, substances, e.g. urine, is prevented from leaking out of the reservoir. Therefore, the connection between the distal end of the package and the reservoir may be adapted to allow the liquid substance to flow only in a direction from the package to the reservoir. As an example, the connection may be provided with a one way valve or closure of the kind known in the art.

After catheterisation, many users would prefer to empty the reservoir before the catheter assembly or reservoir is disposed. It is therefore an advantage to provide a draining spout or valve for emptying the reservoir. The valve should at least be operable between a closed and an open position. As an example, the valve could be a formed as a spout with a passage which is closed. The passage may as an example be closed by melting the reservoir together along a tear-off line. After completion of the catheterisation, the user simply tears off the tip of the spout and empties the reservoir.

In some cases, the user may have to carry a used catheter assembly with an emptied reservoir until an appropriate place of disposal is available. It is therefore an advantage to provide a draining spout with a closure enabling the user, after emptying the reservoir, to close it tightly. As an alternative to a detachable closure, a valve having an open and closed position may be connected to the spout. As an example, the valve may be a regular valve 2-way-valve with an open and closed position.

According to a second aspect, the present invention relates to a catheter assembly comprising a urinary catheter defining a conduit and having a proximal end adapted for insertion into the urinary canal of an individual and an opposite distal end, and a catheter package having a generally tubular body such as a hose with a cavity for accommodation of the catheter. A proximal end of the catheter package includes a catheter cutlet adapted to dismantle or project the proximal end of the catheter from the catheter package. In an opposite distal end of the package is an opening being closed by closing means connected to said catheter for causing opening of the package upon removal of the catheter from the package. This aspect may be combined with any combination of embodiments and aspects described for the first aspect of the present invention.

According to a third aspect, the present invention relates to a catheter assembly comprising a urinary catheter defining a conduit and having a proximal end adapted for insertion into the urinary canal of an individual and an opposite distal end, and a catheter package having a hose with a cavity for accommodation of the catheter and, in a proximal end thereof, a catheter outlet adapted to dismantle or project the proximal end the catheter from the catheter package. The hose is provided with a variable length, allowing the hose to be contracted for exposing the proximal end of the catheter through the catheter outlet, and any combination of embodiments and aspects described for the first aspect of the present invention.

BRIEF DESCRIPTION OF THE DRAWINGS

Preferred embodiments of the invention will now be described in details with reference to the drawing in which:

FIG. 3 shows yet another alternative embodiment of the assembly of FIGS. 1 and 2, and FIG. 4 an embodiment of the assembly, wherein the passage between the catheter and the hose is sealed over a first dismantling period and open over a second dismantling period.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Referring to FIG. 1, a catheter assembly according to the present invention comprises a urinary catheter 1 defining a conduit 2 for transportation of urine and other liquid substances, a catheter package 3 and sealing means 4. In this respect the catheter is defined by a hose and by additional parts connected to the hose, e.g. the plug 25. The plug combines the sealing between the catheter and the package and the closing means adapted to close the distal end of the package—see the following description. The catheter is provided with a proximal end 5, adapted for insertion into the urethra of an individual. The catheter is provided with holes 6 arranged peripherally around the proximal end part of the catheter for draining urine from the bladder and into the conduit of the catheter. The catheter is further provided with at least one opening 7 in the opposite distal end for draining liquid substances out of the conduit. The package is provided with a hose 9 defining a cavity 10 for accommodation of the catheter.

The sealing means 4 is arranged between the outer surface 11 of the catheter and the inner surface 12 of the hose member and provides a substantially liquid tight division of the space confined between the hose member and the catheter into a lower receptacle 13 and an upper receptacle 14.

As shown in FIG. 1, the sealing means may preferably be provided in the form of a radially outwardly extending protrusion 4, e.g. in the form of a soft, resilient vane of the catheter or attached to the catheter and provided in a length which enables the vane to contact the inner surface of the hose member.

Figure 1A:
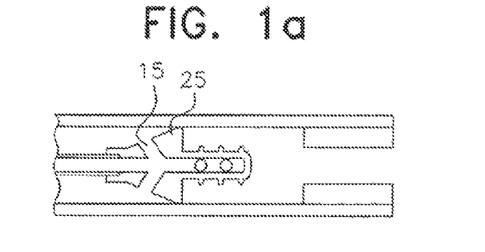
FIG. 1 shows a catheter assembly according to a preferred embodiment of the present invention.

FIG. 1a shows a preferred embodiment of the assembly, wherein a flow channel 15 is provided in order to allow a liquid substance to flow from the upper receptacle 14 and into the conduit 2, e.g. water or a water/saline solution contained in the upper receptacle for treatment of a hydrophilic catheter or a lubricant for causing a low friction surface character of a conventional catheter.

Figure 1B:
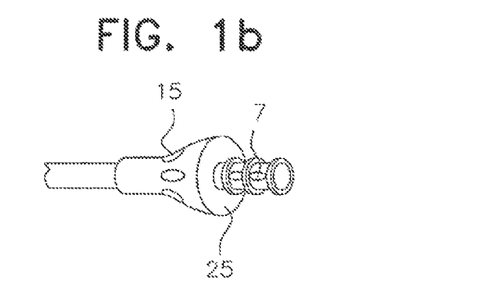

FIG. 1b shows one embodiment of the sealing means connected to the catheter.

Figure 1C:
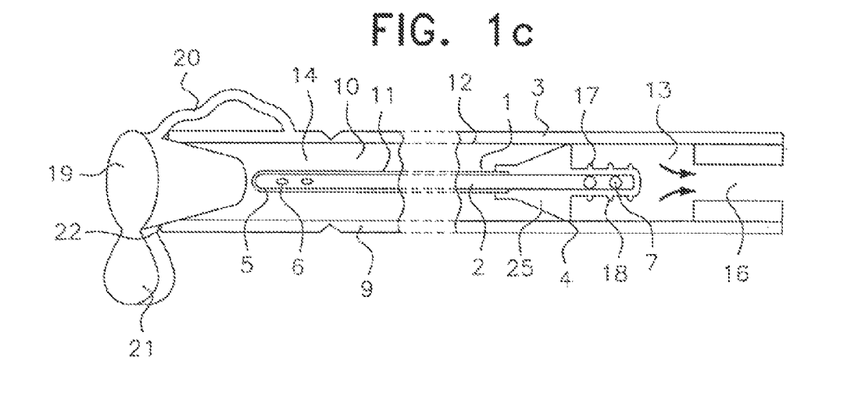

FIG. 1c shows a situation wherein an opening 16 provided in the distal end of the package, allows liquid substances comprised in the lower receptacle to drain out of the package.

Figure 1D:
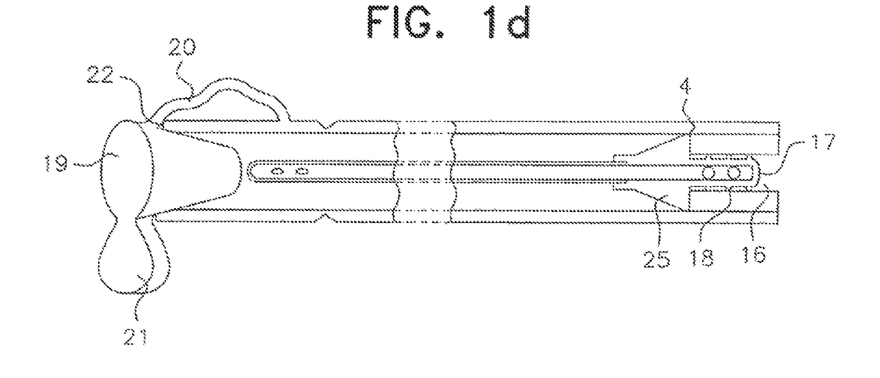

FIG. 1d shows a situation wherein closing means 17 of the catheter liquid tightly seals the opening 16. Preferably, the closing means is provided with a number of resilient and/or soft bulges 18 adapted to contact the inner surface of the opening 16.

FIGS. 1c and 1d further show a detachable closure 19 of the catheter outlet 22 at the proximal end of the package. The closure may, as indicated in FIGS. 1c and 1d, preferably be attached to the package via a strip 20, so that the assembly remains as one unit. The closure may be provided with a radially extending gripping handle 21, easing the removal of the closure, not least for individuals with a reduced dexterity.

FIGS. 2a, 2b, 2c and 2d shows an alternative embodiment of the plug 25 and an alternative embodiment of the distal package end, wherein an open distal end of the package is closed by a closure 26. The closure may either be detachable or glued onto the hose member 9. The plug is preferably provided with at least one outlet opening 27 allowing urine flowing from the bladder and into the proximal end of the catheter to drain out of the catheter through the plug. The plug may further be provided with an inlet 28 for draining a liquid substance from the upper receptacle 14 and into the conduit 2. The closure 26 is further provided with an opening 29 for draining liquid substances out of the lower receptacle, e.g. urine.

Figure 2A:
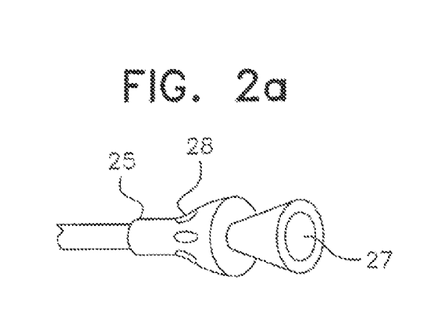
FIG. 2 shows an alternative embodiment of the assembly of FIG. 1.
Figure 2B:
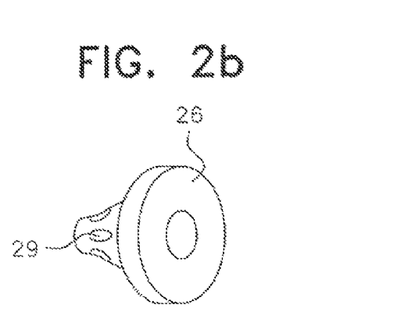
Figure 2C:
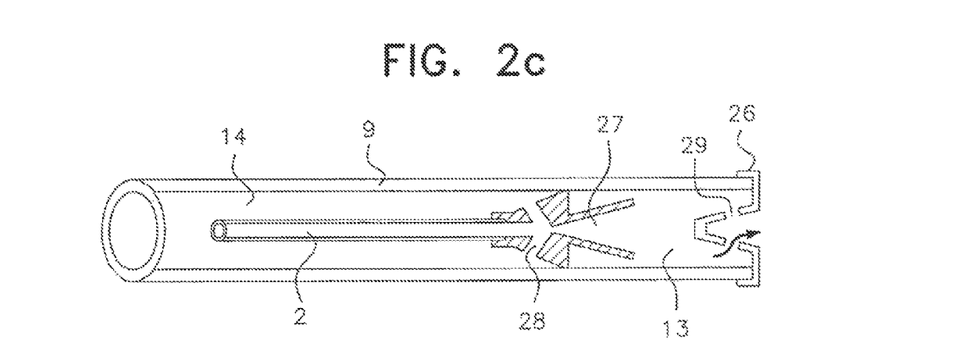

FIG. 2c shows a situation wherein the closing means of the catheter is withdrawn from the closure, whereby the passage 29 is opened.

Figure 2D:
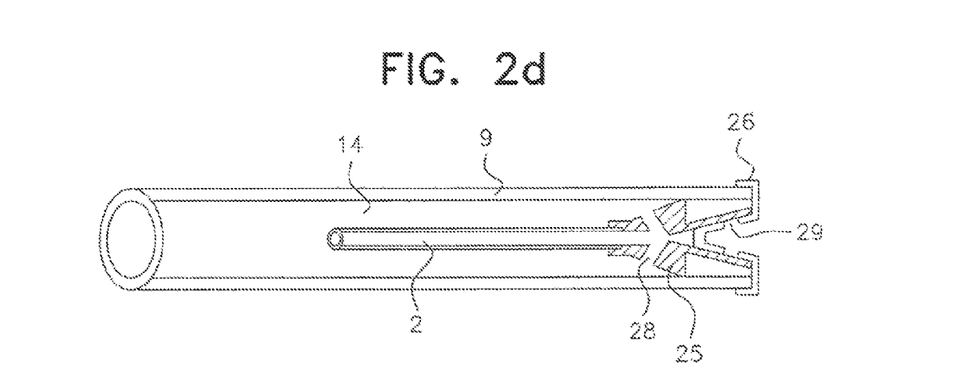

FIG. 2d shows a situation wherein the closing means of the catheter, closes the passage 29 and thereby prevents a liquid substance to drain out of the package.

The catheter and package shown in FIG. 2 is not drawn in its full length. The proximal ends of both have been omitted in order to focus only on the differences between the embodiment of FIG. 1 and FIG. 2.

FIG. 3 shows an embodiment of the invention wherein the plug 35 is provided with features similar to the plug 25 of FIG. 2. The plug further comprises a groove 36 adapted to engage a ring shaped sealing member 37. The ring shaped, sealing member is provided inside the package 38, either fixed to the inner surface of the hose or movably arranged so that it is allowed to slide back and fourth in the hose.

Figure 3A:
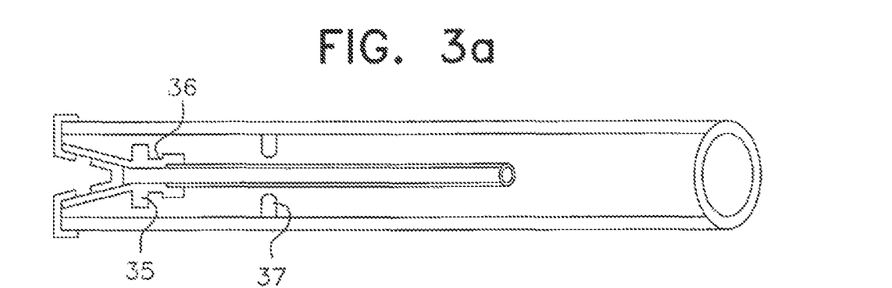
Figure 3B:
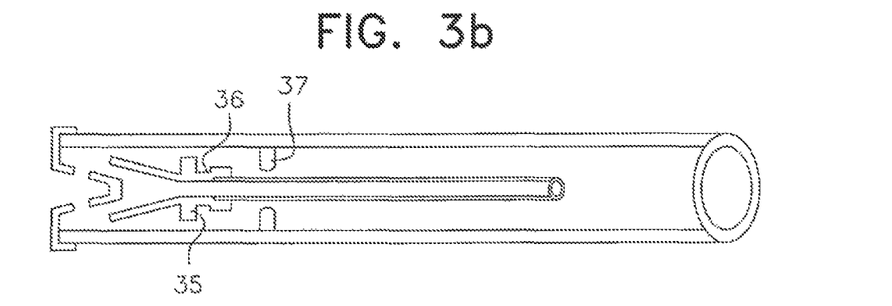
Figure 3C:
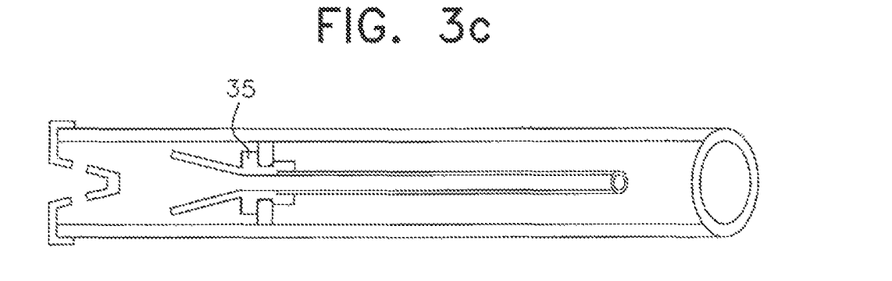
Figure 3D:
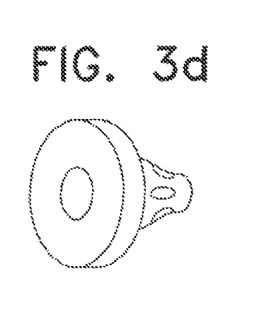
Figure 3E:
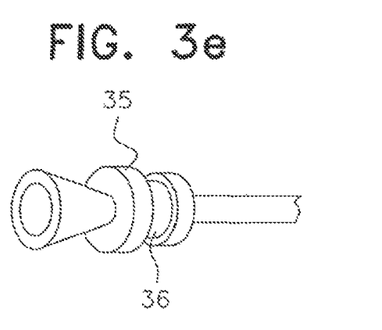
Figure 4A:
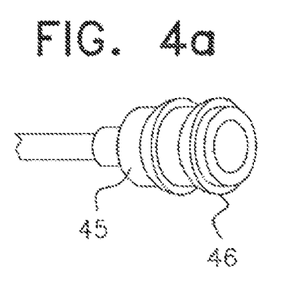
Figure 4B:
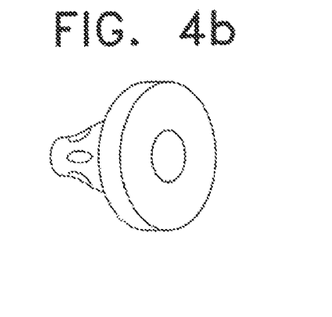
Figure 4C:
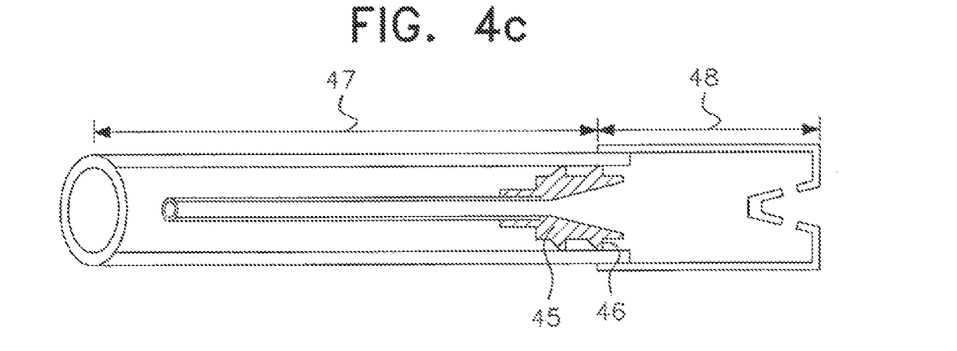
Figure 4D:
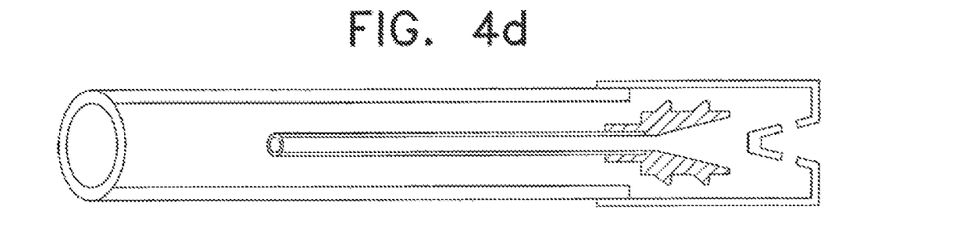
Figure 4E:
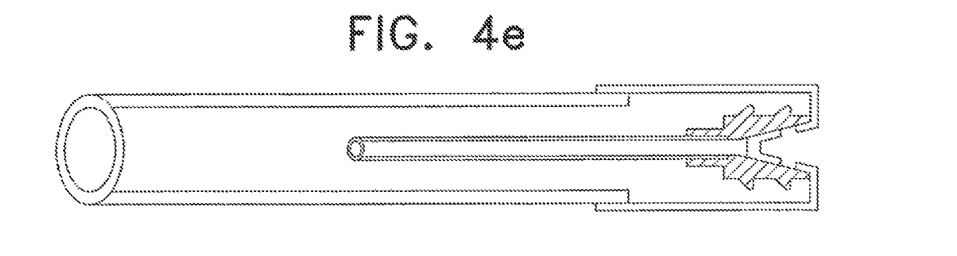
Figure 5A:
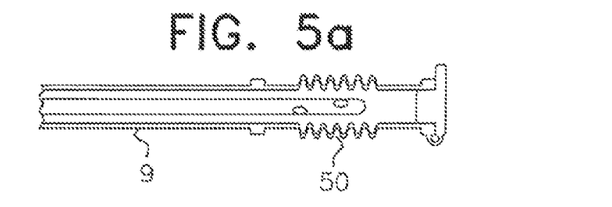
FIG. 5 shows 7 sequences of the removal of a catheter from the assembly by user of a hose with a variable length.
Figure 5B:
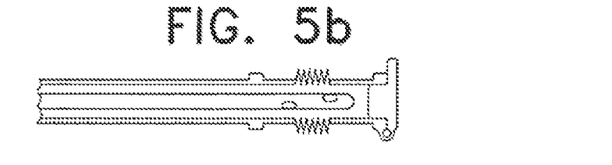
Figure 5C:
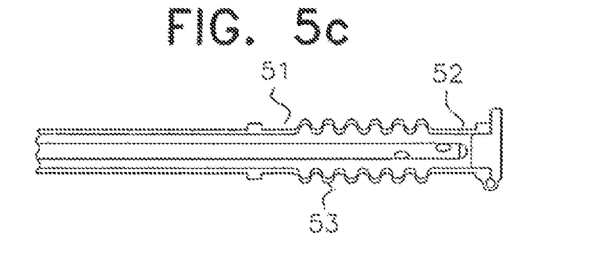
Figure 5D:
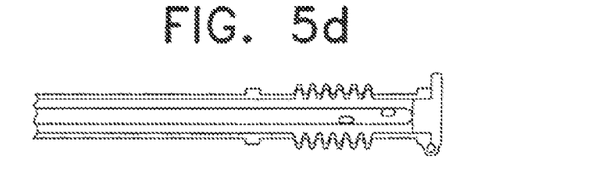
Figure 5E:
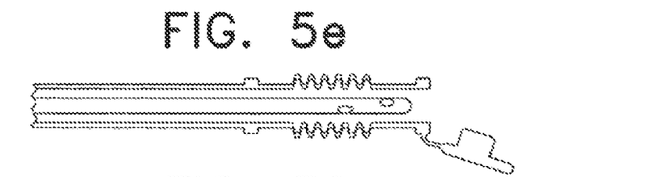
Figure 5F:
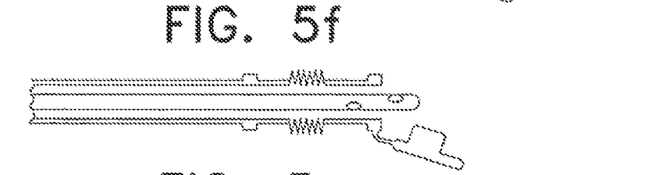
Figure 5G:
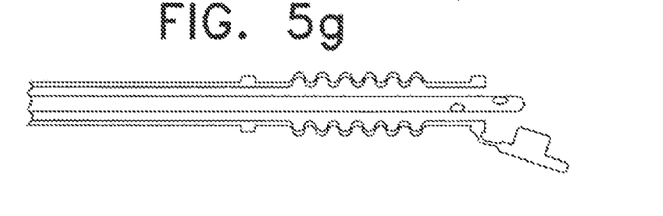

FIG. 3c shows a situation wherein the ring shaped member engages the groove

Likewise FIG. 2, the proximal ends of both the catheter and the package have been left out, in order to focus only on the differences between the embodiment of FIG. 2 and FIG. 3.

FIG. 4 shows an embodiment of the invention where the plug 45 comprises is provided with resilient vanes 46 provided with a diameter so that they over a first section 47 of the hose may contact the inner surface, when the plug is positioned within this section of the hose. However, the hose is provided with two different radial sizes. Accordingly, since the radial size of a second section 48 of the hose is larger than the radial size of the first section of the hose, the vanes 46 can not contact the inner surface of the hose, when the plug is positioned within the second section.

FIG. 5 shows an embodiment of the invention wherein the hose 9 is provided with a variable length. The variable length is provided via a concertina folded wall part 50 of the hose. The hose further forms two gripping zones 51,52 allowing the user to firmly grip the hose and shorten the length thereof, see e.g. FIG. 5b. As shown in the FIGS. 5a, 5b, 5c, 5d, 5e, 5f and 5g, the variable length allows the user to push the proximal catheter end out of the package by shortening the hose length, gripping the catheter through the hose wall, extending the hose length while the catheter is being gripped, releasing the grip and again shortening the length and vice versa. Accordingly, the hose wall 53 may preferably be made from a flexible material allowing the wall to be squeezed into contact with the catheter by finger pressure.

FIG. 6 shows an embodiment of the invention, wherein a compartment 60 is closed in a first end 61, whereas in a second opposite end 62 it is detachably connected with the hose member 63. The compartment is provided with two gripping zones 64,65 enabling the user to firmly grip the compartment. Moreover, the compartment is provided with a concertina folded wall section 66 enabling the user to reduce the length of the compartment, in order to push the proximal end of the catheter 67 out of the proximal end of the package. The closure 69 for closing the first end, is provided so that the package may be closed after the catheterisation. This will allow the user to store the used catheter assembly without any risk of contamination of the surroundings. However, as previously described, the first end 61 may also be closed by a tear-off compartment end, e.g. in the form of a thin foil glued to the end of the compartment.

Figure 6A:
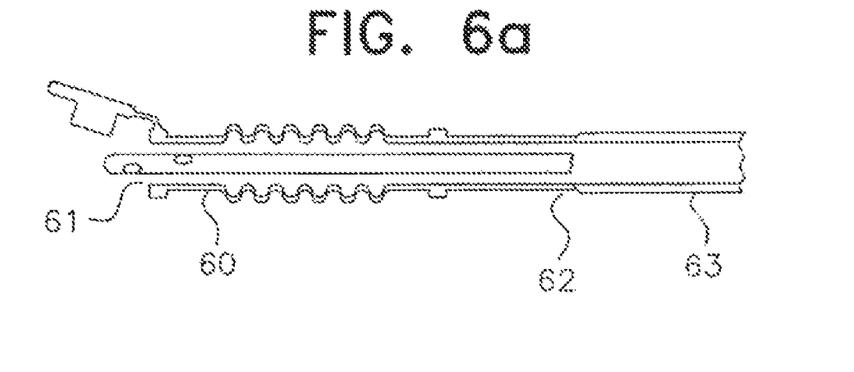
FIG. 6 shows three different embodiments of the invention wherein the a compartment for non-contaminated insertion of the catheter into a urinary canal is attached to the hose member.
Figure 6B:
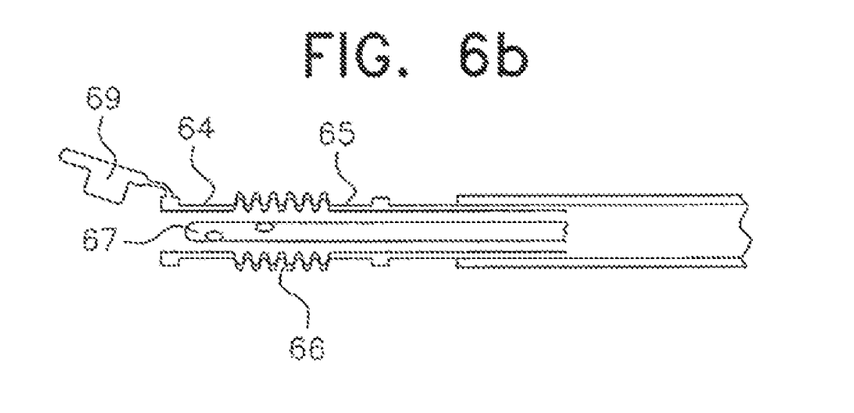
Figure 6C:
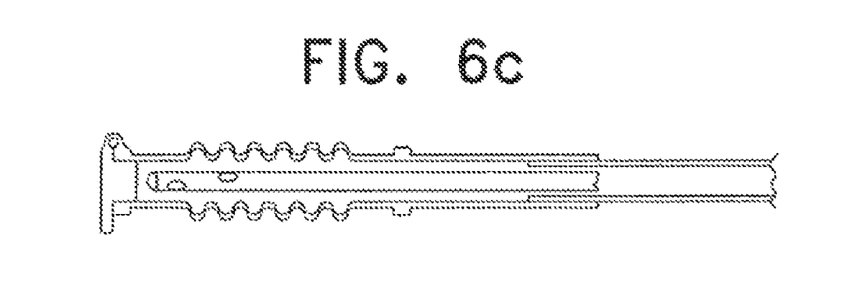

The compartment may be detachably connected to the hose over a tear-off line, see FIG. 6a or alternatively, the compartment may be connected to the hose member telescopically, by inserting one of either the hose or the compartment into the other one of the hose or the compartment, see FIGS. 6b, 6c.

Figure 7A:
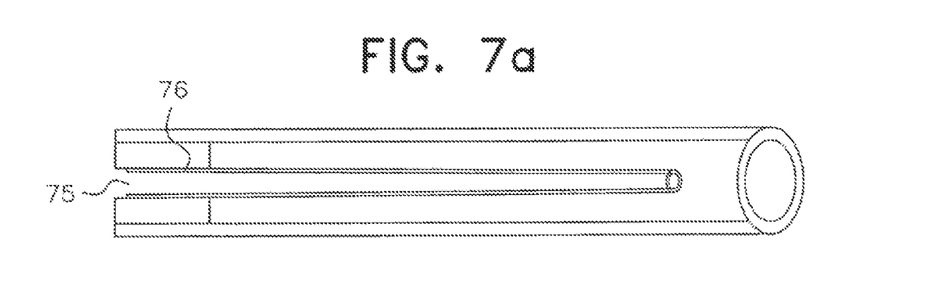
FIG. 7 shows a simple embodiment of the invention, wherein the distal end of the package is closed by the distal end of the catheter itself.
Figure 7B:
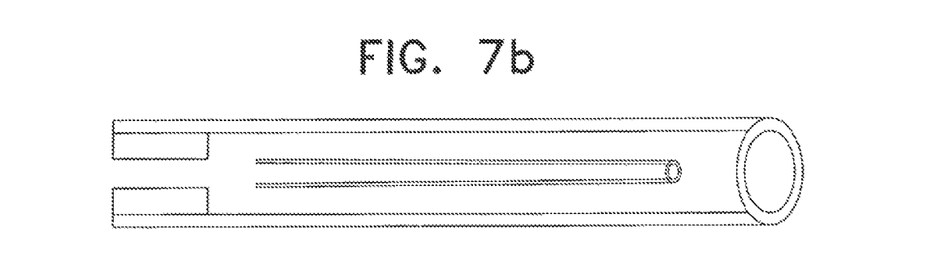
Figure 7C:
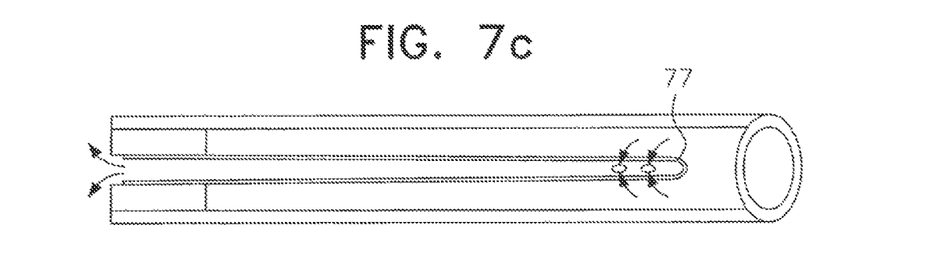

FIG. 7 shows a simple embodiment of the invention wherein the package, in its distal end is provided with an opening 75. The opening may be closed by the distal end 76 of the catheter itself, whereby the distal end of the package is automatically opened upon removal of the catheter from the catheter package. As indicated, a liquid substance comprised in the package, e.g. a liquid swelling medium for treatment of a hydrophilic catheter, is allowed to drain out of the package through the holes 77 provided in the proximal end of the catheter. The proximal end of the catheter and package is, for simplification of the drawing, left of the FIGS. 7a and 7b. In FIG. 7c, the proximal end of the package is left out. However, the proximal end of the package may be closed e.g. by a closure of any kind.

Figure 8A:
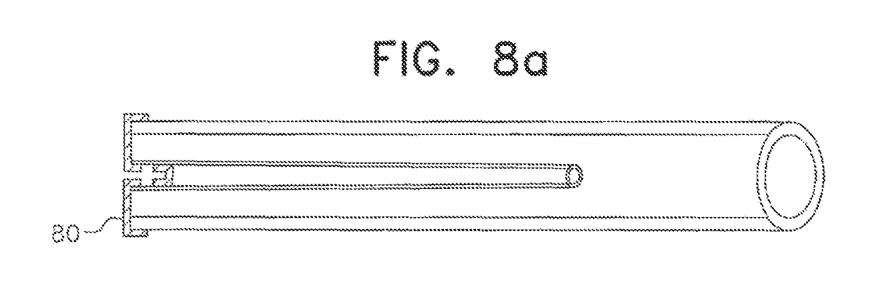
FIG. 8 shows an embodiment of toe assembly shown in FIG. 7, wherein the distal end of the package is closed by a detachable closure.
Figure 8B:
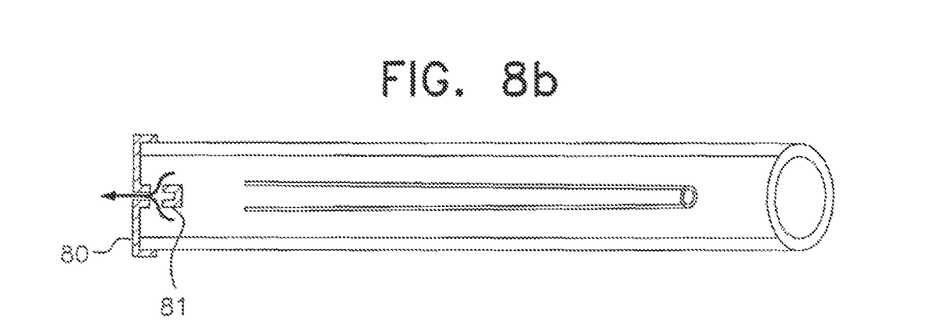
Figure 8C:
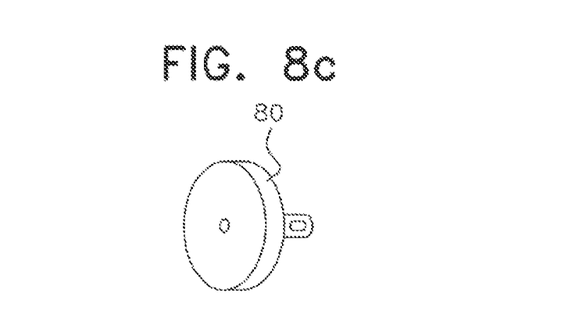

FIG. 8 shows an embodiment of the invention, wherein the distal end of the package is closed by a detachable closure 80. The closure is provided with an outlet 81 for draining liquid substances out of the package. In a first position of the catheter in relation to the package and the closure, see FIG. 8a, the outlet is closed by the distal end of the catheter. When the catheter is removed from the package, the outlet is opened, whereby liquid substances is drained out of the package.

Figure 9:
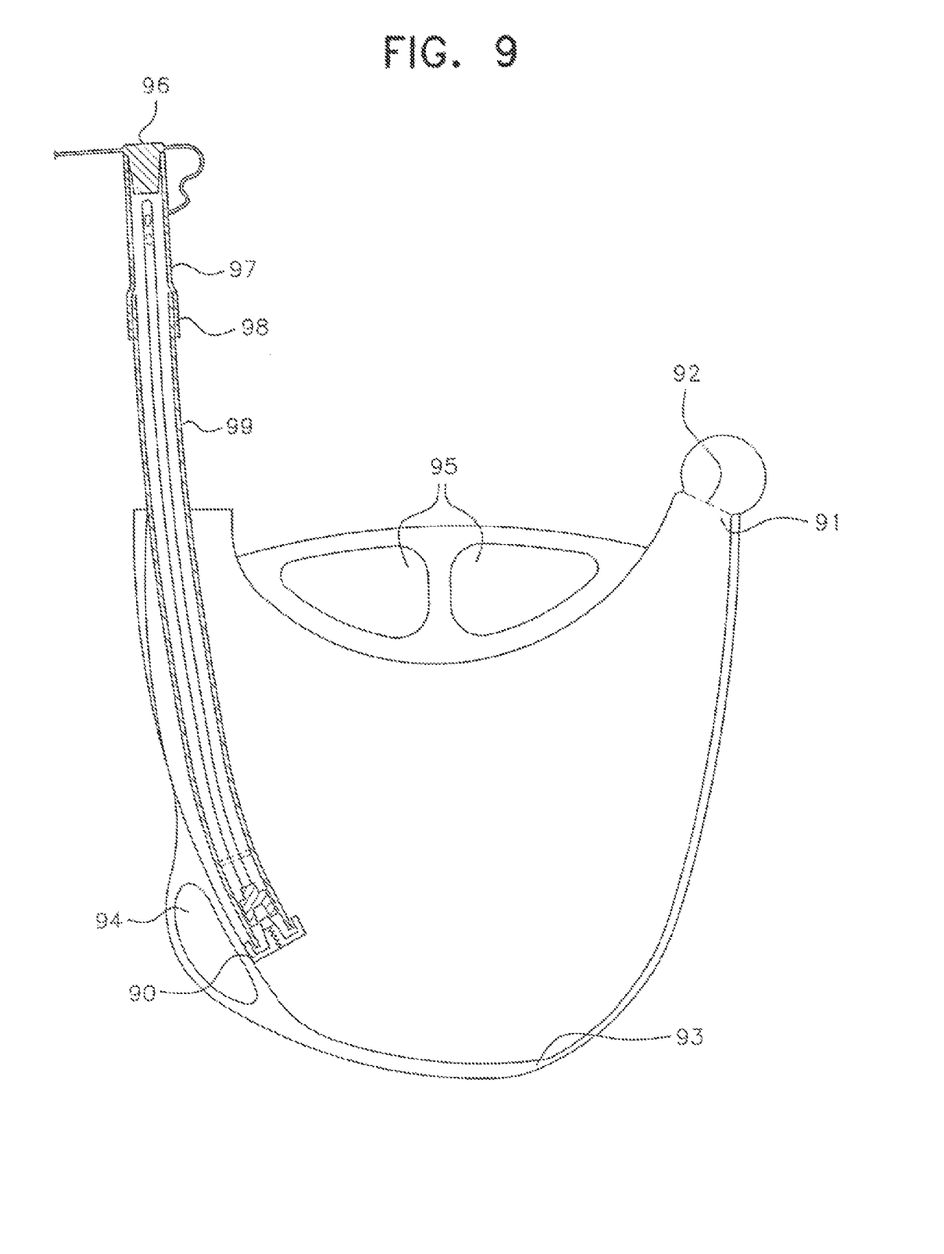
FIGS. 9-11 shows three different embodiments of an assembly comprising a reservoir for storage of urine and other liquid substances.
Figure 10:
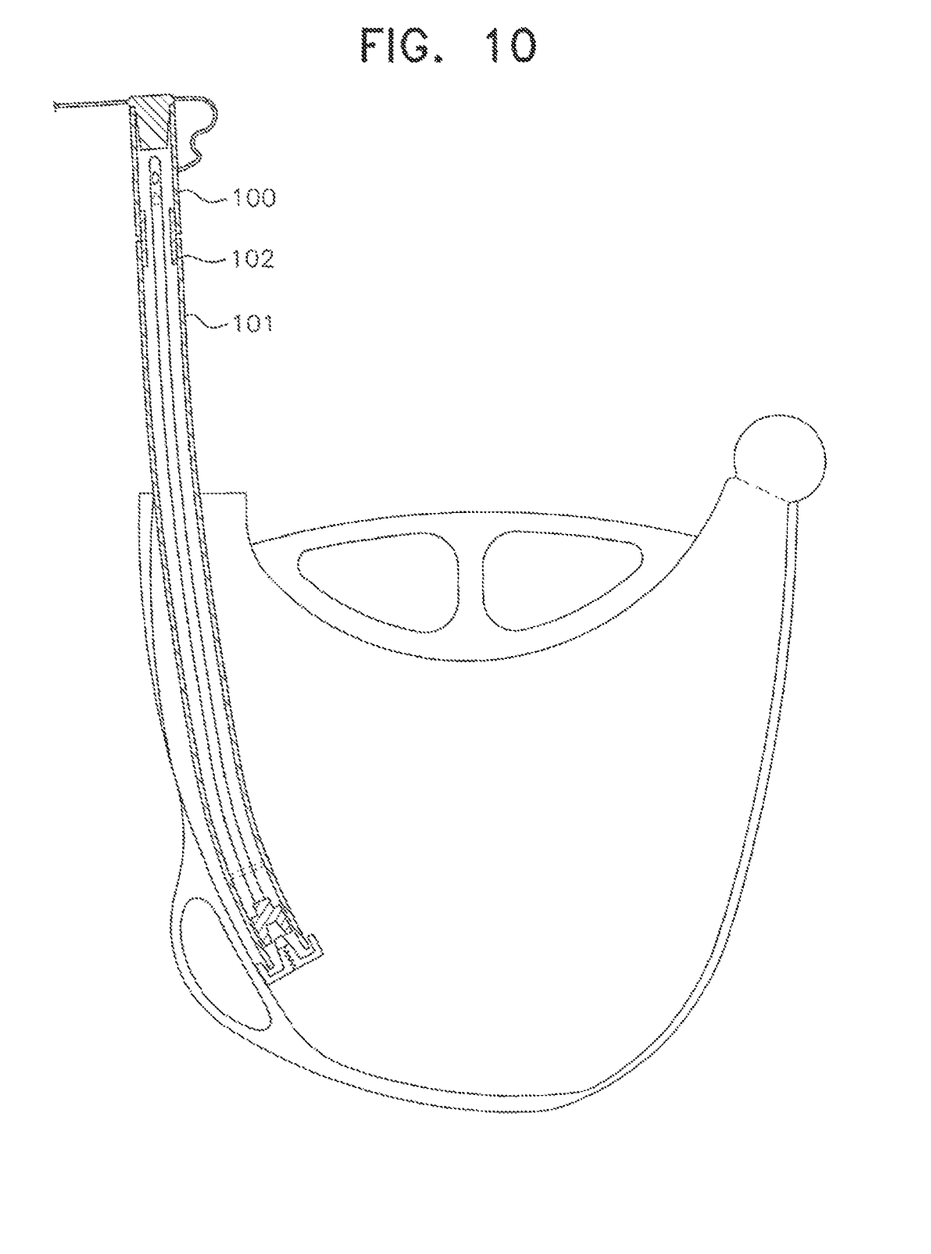
Figure 11:
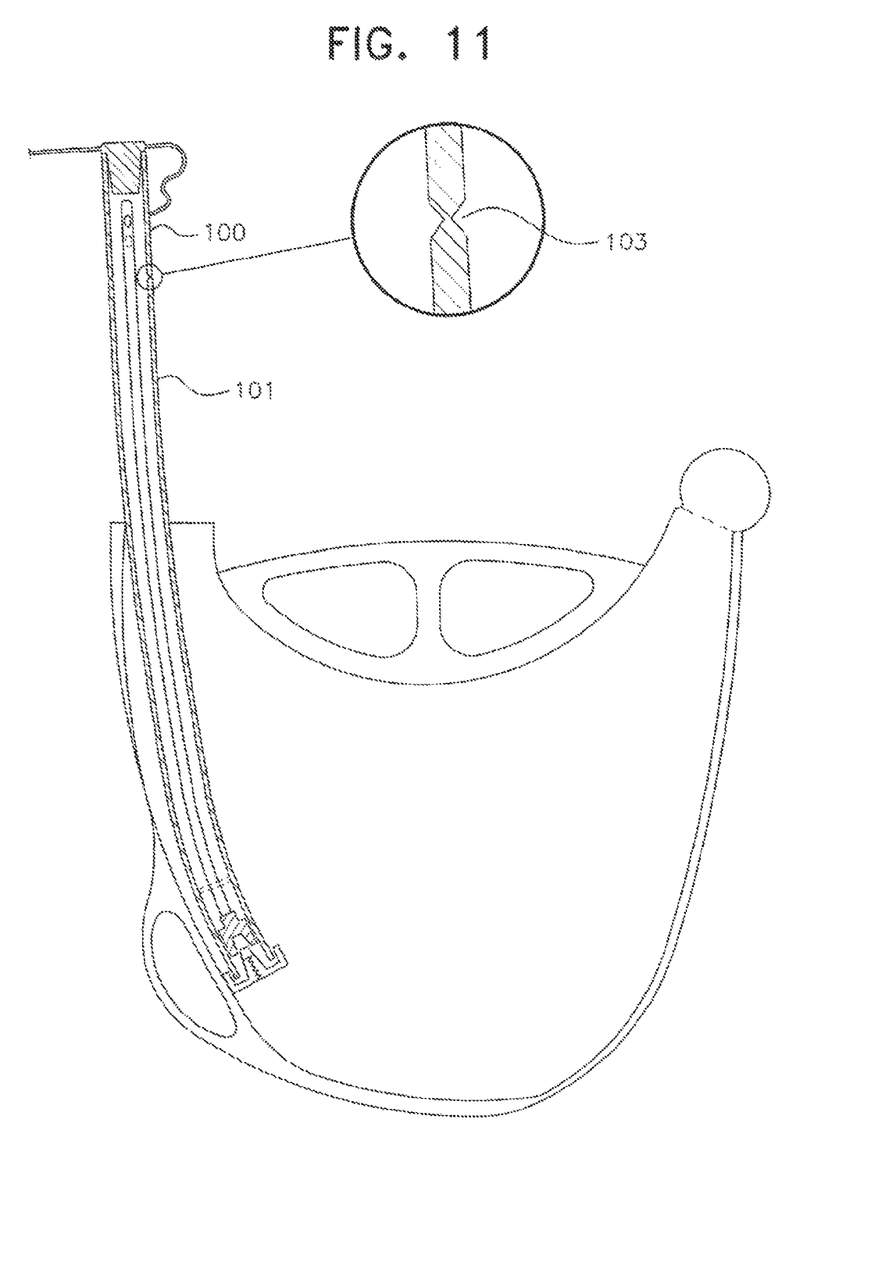

FIGS. 9-11 shows different embodiments of the invention wherein the hose member is connected to a reservoir for collection of liquid substances, e.g. for collection of urine and/or a saline solution having been used for establishing a low friction surface character of the catheter prior to use.

Referring to FIG. 9, the valve 90 may preferably be provided as a one-way closure, so as to ensure that liquids drained into the reservoir does not flow back through the hose member and/or through the catheter. The reservoir is provided with a draining spout or valve 91 for draining the liquid substances out of the reservoir. As an example, the draining valve may be opened by tearing off a top part of the valve. For this purpose the reservoir may preferably be provided with a weakening line 92. The reservoir may preferably be formed as a bag with a substantially flat bottom part 93.

Thereby it will be possible for the user to leave the reservoir on a flat surface, e.g. on the floor, while catheter is inserted into the urethra and while urine is drained into the reservoir. Instructions relating to the opening of the draining valve may preferably be printed on the reservoir. The handles 94, 95 gives the user a better grip, e.g. when emptying the reservoir. For this purpose, it will be specifically appropriate to use both handles in combination, so that the reservoir is lifted in the top handles 95, while the rear handle 94 is used to rotate the reservoir. In this respect it should be kept in mind that the user would typically be at least partly motorically disabled. The assembly further comprises a closure 96 for opening and closing the assembly, respectively. FIG. 9 shows an embodiment of the combined assembly and reservoir, wherein a compartment 97, in the joint 98 is telescopically joined to the hose 99.

FIG. 10 shows an embodiment of the assembly 9, wherein a compartment 100 is attached to the hose member 101 by means of a coupling 102.

FIG. 11 shows an embodiment of the assembly of FIG. 10, wherein the compartment 100 is attached to the hose member 101 by means of a weakened tear-line 103.

It should be understood that the shown embodiments of the assembly wherein the catheter assembly and a reservoir. However, the reservoir may be used independently from the catheter assembly. As an example, a similar reservoir as shown in FIGS. 10-13 may be used in connection with indwelling catheters or in connection with any other kind of catheters, e.g. as a leg-bag, attached to the leg via. leg-straps.

The invention being thus described, it will be apparent that the same may be varied in many ways. Such variations are not to be regarded as a departure from the spirit and scope of the invention, and all such modifications as would be recognized, by one skilled in the art are intended to be included within the scope of the following claims.

What is claimed is:

1. A catheter assembly allowing for non contaminated insertion of the catheter into a urinary canal, said assembly comprising:
a urinary catheter defining a conduit and having a proximal end adapted for insertion into a urinary canal of an individual and an opposite distal end;
a closed tubular catheter package defining a cavity, the urinary catheter retained in the cavity of the closed tubular catheter package, the closed tubular catheter package defining a catheter outlet formed in a proximal end thereof and including a cap closing the catheter outlet, the proximal end of the catheter movable through the catheter outlet of the catheter package when opened; and
a sealing structure connected to the urinary catheter, the sealing structure adapted to slide relative to the tubular catheter package and provide a substantially liquid tight seal between the tubular catheter package and the urinary catheter while the catheter is being dismantled.

2. The catheter assembly according to claim 1, wherein the cap is a removable cap.

3. The catheter assembly according to claim 1, wherein the sealing structure is arranged between an outer surface of the urinary catheter and an inner surface of the generally tubular body, the cavity thereby defining an upper receptacle located near the proximal end of the package and an oppositely located lower receptacle between the catheter and the generally tubular body.

4. The catheter assembly according to claim 1, wherein the sealing structure includes a radially outwardly extending protrusion of the outer surface of the catheter.

5. The catheter assembly according to claim 1, wherein the sealing structure includes at least one radially inwardly extending protrusion of the inner surface of the generally tubular body.

6. A catheter assembly according to claim 1, wherein the sealing structure is adapted to provide a substantially liquid tight seal between the catheter package and the catheter, while a first length of the catheter is being dismantled over a first dismantle period.

7. The catheter assembly according to claim 6, wherein the substantially liquid tight seal is provided continuously between the catheter package and the catheter over the first dismantle period.

8. The catheter assembly according to claim 1, wherein the tubular catheter package includes a gripping zone on an exterior surface of the tubular catheter package.

9. The catheter assembly according to claim 1, wherein
a distal end of the tubular catheter package includes an opening, the opening closed by a closing structure connected to the urinary catheter retained in the cavity of the closed tubular catheter package, the opening configured to open upon projection of the proximal end of the urinary catheter from the tubular catheter package.

10. A catheter assembly according to claim 9, wherein the closing structure is the distal end of the urinary catheter.

11. The catheter assembly according to claim 9, wherein the catheter has an outer surface part treated with a friction-reducing substance.

12. The catheter assembly according to claim 11, wherein the tubular catheter package defines a liquid tight receptacle retaining the friction-reducing substance.

13. The catheter assembly according to claim 9, wherein the closing structure connected to the urinary catheter is provided with a flow channel co-operating with an outlet provided in the tubular catheter package so as, in a first position of the closing structure in relation to the outlet, to prevent a liquid substance to flow from the conduit of the catheter and out of the package.

14. The urinary catheter assembly according to claim 13, wherein the outlet and the flow channel are provided so as, in a second position of the closing structure in relation to the outlet, to allow a liquid substance to flow from the conduit of the catheter and out of the package.

15. The urinary catheter assembly according to claim 13, wherein the flow channel of the closing structure further includes at least one inlet allowing a liquid substance to flow from the receptacle to the conduit of the catheter.

* * * * *